United States Patent [19]

Mallouk et al.

[11] Patent Number: 4,902,308
[45] Date of Patent: Feb. 20, 1990

[54] COMPOSITE MEMBRANE

[76] Inventors: Robert S. Mallouk, Box 332, R.D. #1, Chadds Ford, Pa. 19317; Phillip A. Branca, 132 Country Flower Rd., Newark, Del. 19711

[21] Appl. No.: 206,884
[22] Filed: Jun. 15, 1988
[51] Int. Cl.⁴ .............................................. B01D 53/22
[52] U.S. Cl. ....................................... 55/16; 210/638; 210/500.36
[58] Field of Search .................... 204/296; 55/16, 158; 340/632; 210/638, 500.36

[56] References Cited

U.S. PATENT DOCUMENTS

| | | | |
|---|---|---|---|
| 4,423,157 | 12/1983 | Masuda | 204/296 X |
| 4,490,484 | 12/1984 | Bissut et al. | 204/296 X |
| 4,666,468 | 5/1987 | Wu | 55/16 |

*Primary Examiner*—Frank Spear
*Attorney, Agent, or Firm*—Mortenson & Uebler

[57] ABSTRACT

A porous composite membrane is provided comprising a film of porous, expanded polytetrafluoroethylene whose surfaces, both exterior and within its pores, are coated with a metal salt of a perfluoro-cation exchange polymer. Also provided is the method of avoiding false-positive detection of the presence of organic nerve gas agents by a sensor adapted to detect such presence by employing in the sensor a porous composite membrane comprising a film of porous, expanded polytetrafluoroethylene whose surfaces, both exterior and within its pores, are coated with a metal salt of a perfluoro-cation exchange polymer, the composite acting as a scavenger of unwanted gas components which cause the false-positive signals.

12 Claims, 3 Drawing Sheets

COMPOSITE MEMBRANE

BACKGROUND OF THE INVENTION

1. Field of the Invention

The invention relates to a composite membrane useful as a scavenger of unwanted gas components which cause false-positive detection of organic nerve gas agents in sensors employed for such detection as, for example, by military personnel.

2. Description of Related Art

Organic nerve gas agent sensing devices are employed by military personnel to provide early warning of deadly gases. Such devices are extremely sensitive, being capable of detecting gas concentrations as low as 0.2 micrograms per liter. In addition, in certain industrial applications, the detection of minute concentrations of gaseous components is critical.

In sensing and signaling the presence of certain gases, because of the high sensitivity of sensors used to detect such small concentrations of gas, the presence of other gases in the atmosphere can result in false-positive signals. For example, the presence of small amounts of hydrogen sulfide or hydrogen cyanide gas can set off the alarm in an electronic detecting device which is very sensitively adjusted to detect and signal the presence of minute amounts of phosphorus-containing organic nerve gas agents. Heretofore, these interfering gases have been removed for a time by a scavenging membrane installed within the sensing device.

The conventional scavenging membrane is a composite of polystyrene divinylbenzene copolymer microspheres, whose surfaces are treated to introduce sulfonic acid groups, which microspheres are imbedded in a porous, nonwoven nylon matrix and bound with a polyacrylonitrile/polyvinyl chloride coating. The exposed sulfonic acid groups are ion-exchanged to form the silver salt. The function of the silver salt is to react with and remove the unwanted, interfering gases, such as hydrogen sulfide or hydrogen cyanide, while simultaneously permitting even very minute amounts of the nerve gas agent to be detected to diffuse through the membrane to the sensor.

There are several deficiencies in this scavenging system which contribute to a relatively short active life of the sensor. There is some loss in sensor activity because the nerve gas agent will interact with the styrene divinylbenzene microspheres, with the non-perfluoro organic polymer matrix, or with absorbed water. More importantly, the period of scavenging protection provided is relatively short because a great number, perhaps most of the sulfonic acid groups, are buried in the organic polymer matrix and binder and, consequently, are not available either for silver salt exchange or for subsequent reaction with interfering gases.

The present invention overcomes most of the deficiencies of the conventional scavenging membrane and, suprisingly, has a useful life which can be twice that of the conventional membrane.

SUMMARY OF THE INVENTION

A porous composite membrane is provided comprising a film of porous, expanded polytetrafluoroethylene whose surfaces, both exterior and within its pores, are coated with a metal salt of perfluoro-cation exchange polymer. The perfluoro-cation exchange polymer may be perfluorosulfonic acid polymer or perfluorocarboxylic acid polymer, and the perfluorosulfonic acid polymer is preferred. The metal salt may be a salt of a metal from Group I B of the periodic table of elements or it may be a salt of a polyvalent metal. The metal salt preferably is a silver salt. The perfluoro-cation exchange polymer may have an equivalent weight less than 1000. The base film of porous, expanded polytetrafluoroethylene preferably has a thickness between about 1 mil and about 6 mils, a methanol bubble point as measured by ASTM F316-80 between about 7 and about 26 psi, air flow as measured by Gurley densometer according to ASTM D726-58 between about 3.5 seconds and about 50 seconds and porosity exceeding 60%. The weight fraction of perfluoro-cation exchange polymer preferably exceeds 0.08, based upon the total weight of the composite. The air flow of the composite as measured by Gurley densometer according to ASTM D726-58 can exceed 10 seconds and the thickness of the composite preferably is between about 1 mil and about 5 mils. Most preferably, the air flow is between 12 seconds and 22 seconds, the thickness of the composite membrane is between 1.7 mils and 3 mils and the weight fraction of perfluoro-cation exchange polymer exceeds 0.12, based upon the total weight of the composite.

Also provided is the method of avoiding false-positive detection of the presence of organic nerve gas agents by a sensor adapted to detect the presence of such gases by employing in the sensor a porous composite membrane comprising a film of porous, expanded polytetrafluoroethylene whose surfaces, both exterior and within its pores, are coated with a metal salt of a perfluoro-cation exchange polymer, the composite acting as a scavenger of unwanted gas components which cause false-positive signals.

DETAILED DESCRIPTION OF THE INVENTION AND PREFERRED EMBODIMENTS WITH REFERENCE TO THE DRAWINGS

A porous composite membrane is provided comprising a film of porous, expanded polytetrafluoroethylene whose surfaces, both exterior and within its pores, are coated with a metal salt of a perfluoro-cation exchange polymer. Also provided is the method of avoiding false-positive detection of the presence of organic nerve gas agents by a sensor adapted to detect such presence by employing in the sensor a porous composite membrane comprising a film of porous, expanded polytetrafluoroethylene whose surfaces, both exterior and within its pores, are coated with a metal salt of a perfluoro-cation exchange polymer, the composite acting as a scavenger of unwanted gas components which cause the false-positive signals.

To remedy the deficiencies of conventional membranes, the instant invention provides as a scavenger a porous, expanded polytetrafluoroethylene (PTFE) membrane on whose exterior and interior surfaces a perfluoro-cation exchange polymer is coated and subsequently exchanged to form the silver salt. Porous, expanded polytetrafluoroethylene (PTFE) and the process for its manufacture are disclosed in U.S. Pat. No. 3,953,566, which is incorporated herein by reference. Alternatively, a solution of the silver salt form of the perfluoro-cation exchange polymer can be used to impregnate the expanded PTFE and directly coat the exterior and interior surfaces of the expanded PTFE with the silver salt form of the polymer. What is provided is a thin, chemically inert, microporous support with very high internal surface area for attachment and presentation of the reactive metal ion groups, preferably silver ions. The thickness and tortuosity of the base expanded PTFE can be adjusted within a desired range to permit diffusion of the agent at a rate to maintain good sensitivity with little or no interaction with the matrix. In addition, this structure provides a very high internal surface area and relatively high number of exposed active silver ions per unit membrane area that are available to react with the interfering gases for a longer period and to extend the useful life of the sensor.

According to the invention, although there are only 0.1 to 0.2 times the number of ion exchange groups per unit area than in conventional microsphere loaded structures, the invention provides longer scavenging of interfering gases and can double the life of the sensor. This is a result of the geometry of the invention whereby most of the active ion exchange groups and associated metal ions are available for reaction with interfering gases. In the conventional microsphere loaded structure, a large proportion of the ion exchange groups are buried in the matrix and, consequently, the number and proportion of metal ions per unit membrane area available for reaction with interfering gases is considerably lower than in the membrane of the invention.

Figure 3:
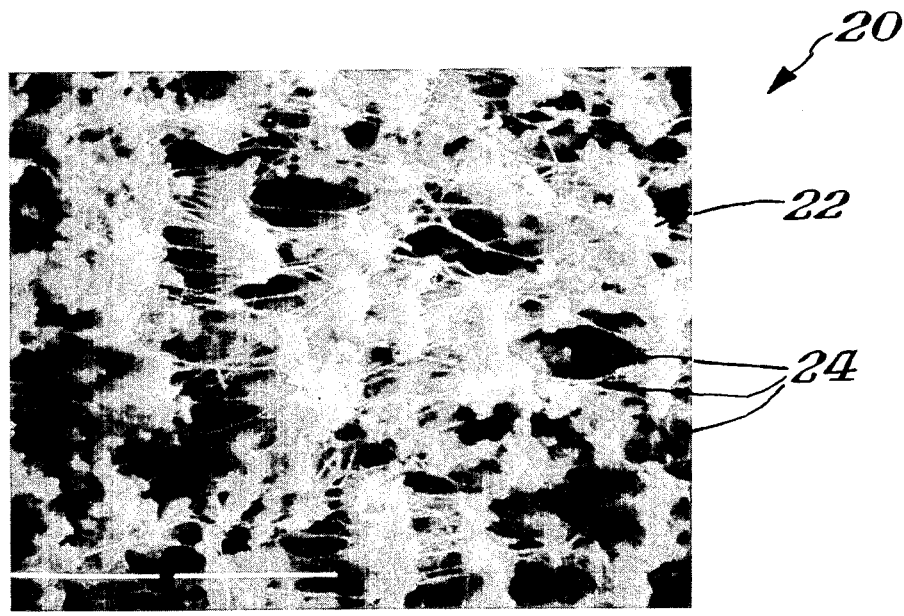
FIGS. 3 and 4 are photomicrographs, taken at 5000×magnification, of the top surface and a cross-section, respectively, of the base film of porous, expanded polytetrafluoroethylene whose surfaces, both exterior and within its pores, are coated with a perfluoro-cation exchange polymer, which forms the intermediate product according to the invention.
Figure 4:
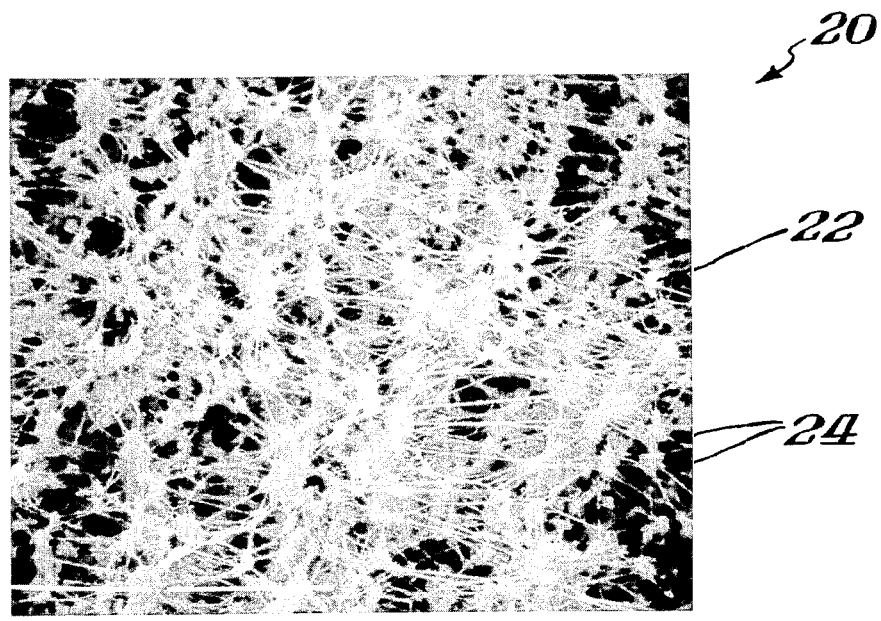

Specifically, an expanded PTFE membrane whose microstructure is comprised of nodes interconnected by fibrils (FIGS. 1 and 2) is used as the support for the active metal ion exchange polymer coating. The expanded PTFE membrane is impregnated with a perfluoro-cation exchange polymer by fully wetting the structure with a dilute solution of this polymer, for example, sulfonic acid or carboxylic acid polymer, in alcohol or other suitable solvent. With the membrane restrained to prevent dimensional changes, the solvent is evaporated in an oven at 80° C. to 120° C. leaving a porous, chemically stable ion to exchange substrate with very high active surface area (FIGS. 3 and 4).

The active cation exchange groups are then converted from the proton form to the desired metal ion form. This is done by first wetting the perfluoro-cation exchange polymer/expanded PTFE substrate with water. This can be facilitated by using a solution of water and alcohol, where the alcohol concentration is high enough to aid in the wetting of the substrate but not so high as to resolubilize the perfluoro-cation exchange polymer. Excess water or alcohol solution is decanted and an aqueous solution of the desired metal salt is added to the perfluoro-cation exchange polymer/expanded PTFE substrate. A large stoichiometric excess of metal ion is added to insure full exchange onto the polymer matrix. Additional conditions such as temperature and pH depend on the nature of the metal ion being added and the type of cation exchange polymer used. Typically the exchange can be carried out at neutral pH and room temperature. The perfluoro-cation exchange/expanded PTFE substrate is exchanged with aqueous metal ion for 10 to 24 hours.

Figure 5:
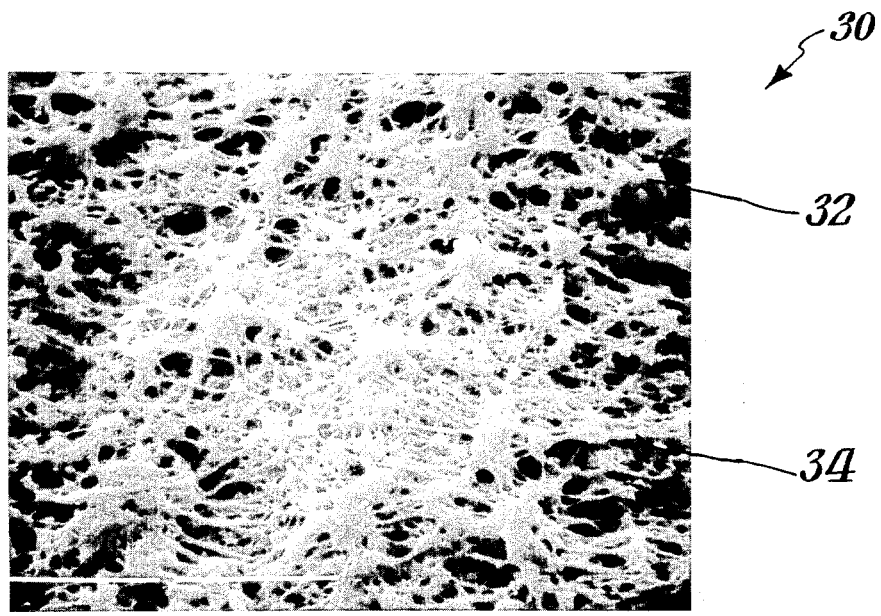
FIGS. 5 and 6 are photomicrographs, taken at 5000×magnification, of the top surface and a cross-section, respectively, of the base film of porous, expanded polytetrafluoroethylene whose surfaces, both exterior and within its pores, are coated with a metal salt of a perfluoro-cation exchange resin, according to the invention.
Figure 6:
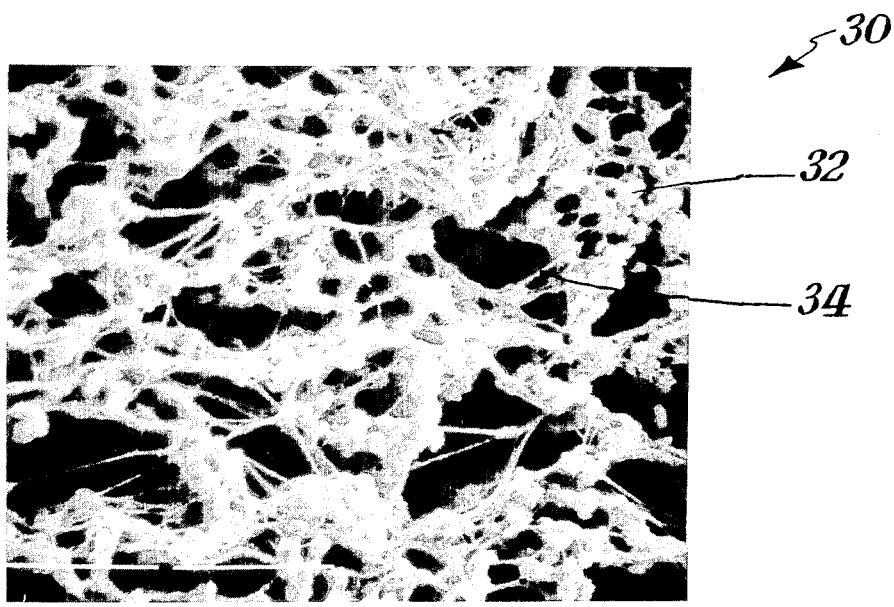

After the metal exchange, excess metal solution is removed and the metal ion/perfluoro-cation exchange polymer/expanded PTFE membrane is rinsed with deionized water. The membrane is restrained while it is dried at room temperature (FIGS. 5 and 6). Vacuum may be employed to speed this process.

After drying, this active metal membrane can be cut to the desired shape and installed in a gas sensor.

EXAMPLE

An expanded PTFE membrane substrate having the following specific physical characteristics was employed: air flow was between 11.6 and 13.0 seconds as measured by Gurley densometer ASTM D726-58; thickness was between 0.0040 and 0.0045 inches; apparent density was between 0.20 and 0.25 g/cc; and methanol bubble point measured according to ASTM F316-80 was between 11.1 and 12.0 psi. A small sample of this expanded PTFE membrane was restrained on a frame. Approximately 10 ml of a 2.0% solution of 920 equivalent weight perfluorosulfonic acid polymer in ethyl alcohol (as disclosed in DuPont U.K. No. 1,286,859) was added to the expanded PTFE substrate to fully wet the membrane. Excess polymer solution was decanted and the wet membrane was placed in 100° C. to 105° C. oven for 5 minutes until fully dry. This perfluorosulfonic acid polymer/expanded PTFE matrix had 12.5% perfluorosulfonic acid polymer by weight, air flow ranged from 9 to 14 seconds measured according to ASTM D726-58, thickness was between 0.0022 and 0.0024 inches, and the sulfonic acid loading was 0.32 microequivalents per square centimeter.

A 2.5 inch square section of perfluorosulfonic acid polymer/expanded PTFE membrane was placed in a polypropylene frame and wet with a solution of 15% isopropyl alcohol in deonized water. Excess alcohol solution was decanted and approximately 10 mil of a 1.0M solution of silver nitrate was added. The membrane was allowed to silver exchange at room temperature overnight. The silver ion exchanged membrane was then rinsed with deionized water and dried at room temperature under vacuum. The dried membrane was cut to give two 1×2 inch samples which were placed into gas sensors.

The interfering gas scavenging membrane was tested for active lifetime by challenging it with a standard atmosphere of hydrogen cyanide. The membrane was installed in a gas sensor and placed in a large standard atmosphere chamber (2 cu. ft.) through which 10 ppm HCN was pumped at 8 liters per minute. Scavenging capability of the membrane was evaluated periodically by removing the sensor from the HCN atmosphere, turning the sensor on in clean air for 2 minutes, moving the sensor to the standard 10 ppm HCN atmosphere and sensing for another 2 minutes, then sensing for another 2 minutes in clean air. A positive response from the sensor indicates that the scavenging capability of the membrane has been exhausted.

The membrane was evaluated for lifetime effectiveness against 10 ppm HCN along with a control representing a conventional membrane (Gelman SA6404, exchanged with silver ion). Three samples of the control were tested. After 30 days of exposure one conventional sample had failed. After 48 days, the remaining two conventional samples had failed. In comparison, four samples of the above Example according to the invention were tested. All four were functioning after 55 days of exposure. Three of the four failed after 63 days of exposure. The fourth failed after 70 days of exposure.

The control had between 2.5 and 6.0 microequivalents/$cm^2$ theoretical active sites whereas the expanded PTFE/perfluorosulfonic acid polymer/silver ion membrane from the Example had only 0.32 microequivalents/$cm^2$ theoretical active sites. In spite of this, the membrane of the Example showed between 31% and 110% increase in lifetime, with less than one-eighth of the theoretical equivalents of the control.

Figure 1:
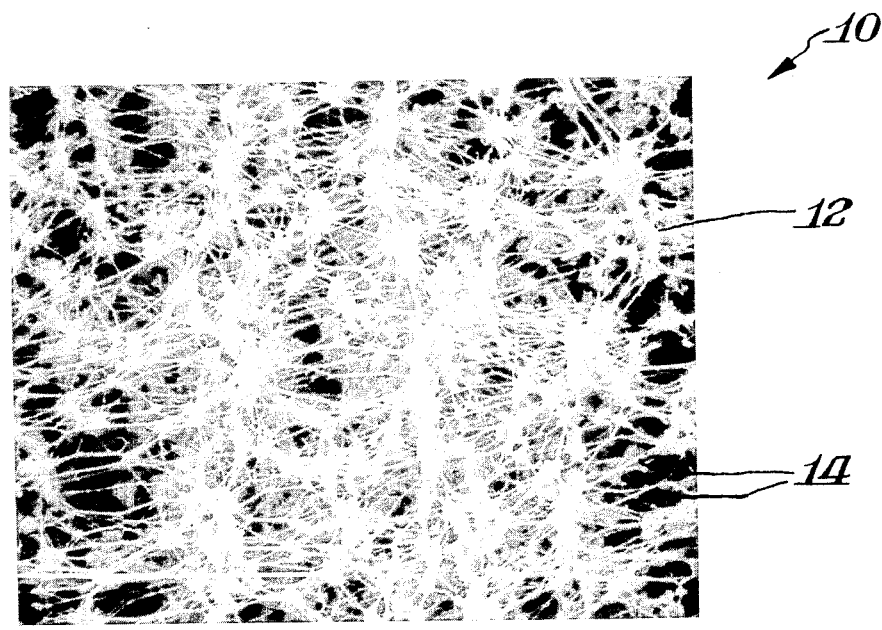
FIGS. 1 and 2 are photomicrographs, taken at 5000×magnification, of the top surface and a cross-section, respectively, of a base film of porous, expanded polytetrafluoroethylene used in the composite membrane of the invention.
Figure 2:
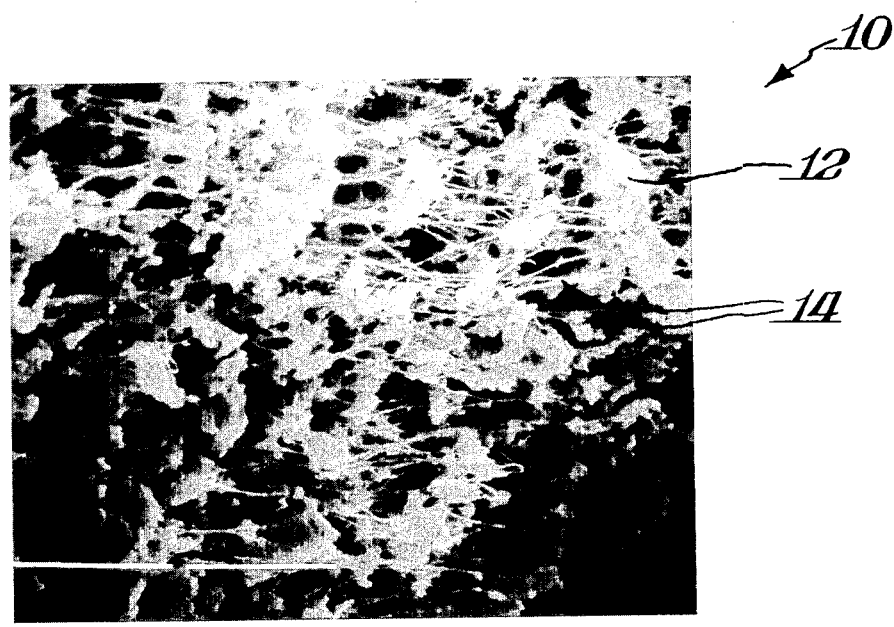

The components according to the invention can be seen in the accompanying drawings wherein FIGS. 1 and 2 are photomicrographs, taken at 5000× magnification, of the top surface and a cross-section, respectively, of a base film of porous, expanded polytetrafluoroethylene used in the composite membrane of the invention. In these figures, the base membrane of porous, expanded polytetrafluoroethylene 10 has a microstructure comprising nodes 12 interconnected by many fine fibrils 14.

FIGS. 3 and 4 are photomicrographs, taken at 5000× magnification, of the top surface and a cross-section, respectively, of the base film of porous, expanded polytetrafluoroethylene whose surfaces, both exterior and within its pores, are coated with a perfluoro-cation exchange polymer, which forms the intermediate product according to the invention. The membrane 20 has nodes 22 and fibrils 24 which are coated with a perfluoro-cation exchange polymer.

FIGS. 5 and 6 are photomicrographs, taken at 5000× magnifiation, of the top surface and a cross-section, respectively, of the base film of porous, expanded polytetrafluoroethylene whose surfaces, both exterior and within its pores, are coated with a metal salt of a perfluoro-cation exchange resin, according to the invention. The membrane 30 has nodes 32 and fibrils 34 coated with a metal salt of a perfluoro-cation exchange polymer. In these photomicrographs, the coating is the silver salt of perfluorosulfonic acid polymer.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. A porous composite membrane comprising a film of porous, expanded polytetrafluoroethylene whose surfaces, both exterior and within its pores, are coated with a reactive metal salt of perfluoro-cation exchange polymer.

2. The composite membrane of claim 1 wherein said perfluoro-cation exchange polymer is perfluorosulfonic acid polymer.

3. The composite membrane of claim 1 wherein said perfluoro-cation exchange polymer is perfluorocarboxylic acid polymer.

4. The composite membrane of claim 1 wherein said-metal salt is a salt of a metal from Group I B of the periodic table of elements.

5. The composite membrane of claim 1 wherein said metal salt is a silver salt.

6. The composite membrane of claim 1 wherein said metal salt is a salt of a polyvalent metal.

7. The composite membrane of claim 1 wherein said perfluoro-cation exchange polymer has an equivalent weight less than 1000.

8. The composite membrane of claim 1 wherein said film of porous, expanded polytetrafluoroethylene has a thickness between about 1 mil and about 6 mils, a methanol bubble point as measured by ASTM F316-80 between about 7 and about 26 psi, air flow as measured by Gurley densometer according to ASTM D726-58 between about 3.5 seconds and about 50 seconds and porosity exceeding 60%.

9. The composite membrane of claim 1 wherein the weight fraction of perfluoro-cation exchange polymer exceeds 0.08, based upon the total weight of the composite.

10. The composite of claim 1 wherein the air flow of the composite as measured by Gurley densometer according to ASTM D726-58 is greater than 10 seconds and the thickness of the composite is between about 1 mil and about 5 mils.

11. The composite of claim 10 wherein the air flow is between 12 seconds and 22 seconds, the thickness of said composite membrane is between 1.7 mils and 3 mils and the weight fraction of perfluoro-cation exchange polymer exceeds 0.12, based upon the total weight of the composite.

12. The method of avoiding false-positive detection of the presence of organic nerve gas agents by a sensor adapted to detect said presence by employing in said sensor a porous composite membrane comprising a film of porous, expanded polytetrafluoroethylene whose surfaces, both exterior and within its pores, are coated with a metal salt of a perfluoro-cation exchange polymer, said composite acting as a scavenger of unwanted gas components which cause said false-positive signals.

* * * * *